United States Patent
Wilson et al.

(10) Patent No.: US 6,749,830 B2
(45) Date of Patent: Jun. 15, 2004

(54) METHOD FOR THE SYNTHESIS OF RADIOLABELED COMPOUNDS

(75) Inventors: Alan Alexander Wilson, Toronto (CA); Armando Francisco Garcia, Toronto (CA); Li Jin, Shoreline, WA (US); Sylvain Joseph Houle, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 185 days.

(21) Appl. No.: 10/059,138

(22) Filed: Jan. 31, 2002

(65) Prior Publication Data

US 2002/0155063 A1 Oct. 24, 2002

Related U.S. Application Data

(60) Provisional application No. 60/265,126, filed on Jan. 31, 2001.

(51) Int. Cl.[7] .............................................. A61K 51/00
(52) U.S. Cl. ................... 424/1.11; 424/1.65; 424/1.81; 424/1.85; 424/1.89
(58) Field of Search ............................. 424/1.11, 1.65, 424/1.81, 1.85, 1.89; 422/159

(56) References Cited

PUBLICATIONS

Crouzel, C. Längström, B., Pike, V.W., and Coenen, H.H. (1987) Recommendations for a practical production of [$^{11}$C] methyl iodide *Appl. Radiat. Isot. Int. J. Appl. Instrum. Part A* 38, 601–603.

Dannals, R.F., Ravert, H.T., and Wilson, A.A. (1990) Radiochemistry of Tracers for Neurotransmitter Receptor Studies. In: *Quantitative Imaging: Neuroreceptors, Neurotransmitters, and Enzymes*. (Edited by Frost, J.J. Wagner Jr., H.N. pp. 19–35,. Raven Press, New York.

Iwata. R., Pascali, D., Yuasa, M., Yanai, K., Takahashi, T., and Ido, T. (1992) On–line [$^{11}$C]Methylation using [$^{11}$C] Methyl Iodide for the Automated Preparation of $^{11}$C–Radopharmaceuticals *Appl. Radiat. Isot.* 43, 1083–1088.

Jewett, D., Ehrenkaufer, R., and Ram, S. (1985) A Captive Solvent Method for Rapid Radiosynthesis: Application to the Synthesis of [1–$^{11}$C]Palmitic Acid *Int. J. Appl. Radiat. Isot.* 36,672–674.

Jewett, D.M. (1992) A Simple Synthesis of [$^{11}$C]Methyl Triflate *Appl. Radiat. Isot.* 43, 1383–1385.

Jewett, D.M., Manger, T.J., and Watkins, G.L. (1991) Captive Solvent Methods for Fast Simple Carbon–11 Radioalkylations. In: *New Trends in Radiopharmaceutical Synthesis, Quality Assurance and Regulatory Control* (Edited by Emran, A.M.) pp. 387–391. Plenum Press, New York.

Langer, O., Nagren, K., Dolle, F., Lundkvist, C., Sandell, J., Swahn, C.-G., Vaufrey, F., Crouzel, C., Maziere, B., and Halldin, C. (1999) Precursor Synthesis and Radiolabeling of the Dopamine D2 Receptor Ligand . [$^{11}$C]Raclopride from [$^{11}$C]Methyl Triflate. *J. Labelled Compd. Radiopharm.* 42, 1183–1193.

Längström, B., and Lundqvist. H. (1976) The preparation of $^{11}$C–methyl iodide and its use in the synthesis of $^{11}$C–methyl–L–methionine *Appl. Radiat. Isot.* 27, 357–363.

Larsen, P., Ulin, J. Dahlstrom, K., and Jensen, M. (1997) Synthesis of [$^{11}$C]Iodomethane by Iodination of [$^{11}$C]Methane *Appl. Radiat. Isot.* 48,53–157.

Link, J.M., Krohn, K.A., and Clark, J.C. (1997) Production of [$^{11}$C]CH$_3$I by single pass reation of [$^{11}$C]CH$_4$ with I$_2$ *Nucl Med Biol* 24, 93–97.

Marazano, C., Maziere, M., Berger, G., and Comar, D. (1977) Synthesis of methyl iodide–$^{11}$C and formaldehyde–$^{11}$C *Appl. Radiat. Isot.* 28, 49–52.

Maziere, B., Coenen, H., Halldin, C., Nagren, K., and Pike, V. (1992) PET radioligands for dopamine receptors and re–uptake sites: chemistry and biochemistry *Nuc. Med. Biol.* 19, 497–512.

McCarron, J.A., Turton, D.R., Pike, V. W., and Poole, K. G. (1996) Remotely–controlled production of the 5–HT$_{1A}$ receptor radioligand, [carbonyl–C–11]WAY–100635, via C–11–carboxylation of an immobilized Grignard reagent *J Labelled Compds. Radiopharm.* 38, 941–953.

Mizuno, K.I., Yamazaki, S., Iwata, R., Pascali, C., and Ido, T. (1993) Improved Preparation of L–[Methyl–C–11]Methionine by on– Line [C–11]*Methylation Applied Radiation and Isotopes* 44, 788–790.

Parker, A. (1969) Protic–Dipolar Aprotic Solvent Effects on Rates of Bimolecular Reactions *Chem. Rev.* 69, 1–33.

Pascali, C., Iwata, R., and Ido, T. (1992) Comparative Study on the Influence of Bases'on (3–N–[C–11]Methyl)Spiperone Synthesis *Int. J. Appl. Radiat. isot.* 43, 1526–1528.

(List continued on next page.)

*Primary Examiner*—Michael G. Hartley
(74) *Attorney, Agent, or Firm*—Kramer & Amado, P.C.

(57) ABSTRACT

The present invention relates to a new method for radiolabeling chemical compounds. The new method attains the goals of simplicity, high radiochemical yields, speed, versatility, and automation. An HPLC injection loop on an HPLC injection valve is loaded with a solution of precursor and the radiolabeling reagent is passed through the loop. The contents of the loop are then quantitatively injected onto the HPLC column for purification. Radiochemical yields are equal to or superior to conventional solution methods in all cases, even though no heat need be applied. Since no vials, transfer lines, cooling, heating, or sealing valves are required, no transfer losses occur, yields are high, and clean-up is minimal. This "loop method" is ideal for the preparation of radiolabeled compounds, in particular those prepared from [$^{11}$C]-iodomethane.

9 Claims, 2 Drawing Sheets

OTHER PUBLICATIONS

Watkins, G., Jewett, D., Mulholland, G., Kitbourn, M., and Toorongian, S. (1988) A Captive Solvent Method for Rapid N–[$^{11}$C]Methylation of Secondary Amides: Application to the Benzodiazepine, 4'–Chlorodiazepam (RO5–4864) *Appl. Radiat. Isot.* 39, 441–444.

Wilson, A.A., DaSilva, J.N., and Houle, S. (1996) In vivo evaluation of [$^{11}$C] and [$^{15}$F]–labelled cocaine analogues as potential dopamine transporter ligands for positron emission tomography *Nucl. Med. Biol.* 23, 141–146.

Wilson, A.A., DaSilva, J.N., and Houle, S. (1996) Solid–phase radiosynthesis of [$^{11}$C]WAY 100635 *J. Labelled Compds. Radiopharm.* 38, 149–154.

METHOD FOR THE SYNTHESIS OF RADIOLABELED COMPOUNDS

This application claims the benefit under 35 USC §119(e) from U.S. provisional patent application Ser. No. 60/265,126, filed Jan. 31, 2001.

FIELD OF THE INVENTION

The invention relates to a method for radiolabeling chemical compounds. Specifically, the method of the invention provides a simple and efficient method to [$^{11}$C]-methylate target substrates.

BACKGROUND OF THE INVENTION

Methylation of suitable precursors with [$^{11}$C]-iodomethane continues to be the workhorse method of synthesis of a majority of positron emission tomography (PET) radiotracers, especially in the area of receptor imaging. Many improvements have been made in the production of [$^{11}$C]-iodomethane, most recently with the introduction of "gas-phase methods" which are highly automated and produce a product with very high specific activity (1,9,10). Efforts to simply and automate the [$^{11}$C]-methylation reaction and purification have been less spectacular. Many attempts to streamline the process have revolved around the idea of eliminating the traditional "solution in reaction vial" whereby [$^{11}$C]-iodomethane is distilled into a vessel containing solvent, precursor, and base/catalyst if required (1,8,11). In this common scenario, cooling of the vessel for trapping [$^{11}$C]-iodomethane is usually required followed by sealing of the vessel, heating to effect reaction, quenching of the reaction, and transferring of the vessel contents to a high performance liquid chromatography (HPLC) system for purification. The streamlining and automation of this sequence of events, especially the last, has proven onerous.

An attractive technique to surmount some of these problems was described in the pioneering papers of Jewett and Watkins on captive solvent chemistry (4,6,17). Their goal was to develop a solid support to trap reagents and iodomethane together, eliminating the need for a reaction vessel with its septa, needles, and their associated problems. Similar efforts have been forthcoming from other groups where the technique has been named on-line, solid-phase, or immobilized techniques (3,14,16,19). When the solid support is plumbed in to take the place of the HPLC sample loading loop then transfer losses from reaction vessel to loop can also be eliminated and the process simplified.

Such captive solvent techniques have not been widely adopted by the field, perhaps because no one method fulfills all the requirements of ease of use reproducibility, and versatility. Some methods have not been fully integrated as part of the HPLC system (17,19), some require non-proprietary solid-supports (6,14), while others can degrade the HPLC purification of the radiotracer (3). In addition, cooling and heating the reaction site are still necessary steps in the synthetic sequence.

There remains a need for a simple, fast and versatile method to radiolabel chemical compounds, specifically via [$^{11}$C]-methylation reactions, which provides high radiochemical yields and is easily automated.

SUMMARY OF THE INVENTION

A new method to radiolabel chemical compounds has been developed. Specifically the method involves the [$^{11}$C]-methylation of chemical compounds. In general terms, the method involves trapping a radiolabeling reagent directly in a standard HPLC loop coated with precursor solution, allowing the reagents to react, and then directly injecting the reaction mixture onto an HPLC purification column. The method does not require the use of any additional solid support nor any heating or cooling.

The present invention therefore provides a method for radiolabeling precursor chemical compounds comprising the steps of:

injecting a sample comprising a precursor chemical compound into an injection loop of a high performance liquid chromatograph (HPLC);

injecting a radiolabeling reagent into the injection loop;

allowing the radiolabeling reagent to react with the precursor chemical compound, to provide a reaction mixture comprising a radiolabeled compound;

injecting the reaction mixture into the HPLC column; and isolating the radiolabeled compound.

In embodiments of the present invention, the radiolabeling reagent is a [$^{11}$C]-methylating reagent. Accordingly, the present invention further provides a method for [$^{11}$C]-methylation of precursor chemical compounds comprising the steps of:

injecting a sample comprising a precursor chemical compound into an injection loop of a high performance liquid chromatograph (HPLC);

passing [$^{11}$C]-iodomethane through the injection;

allowing the [$^{11}$C]-iodomethane to react with the precursor chemical compound, to provide a reaction mixture comprising a [$^{11}$C]-methylated compound;

injecting the reaction mixture into the HPLC column; and isolating the [$^{11}$C]-methylated compound.

Some literature methods for performing [$^{11}$C]-methylation reactions involve the use of a solid support as the means to bring together precursor and [$^{11}$C]-iodomethane. A disadvantage of this is that the reaction mixture is strongly retained by the support with the result that HPLC separations are less efficient (3). Using only the loop as a support avoids this pitfall and no differences in chromatographic separations could be discerned as compared to injections of solutions of reaction mixtures.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

(I) Method of the Invention

Figure 1:
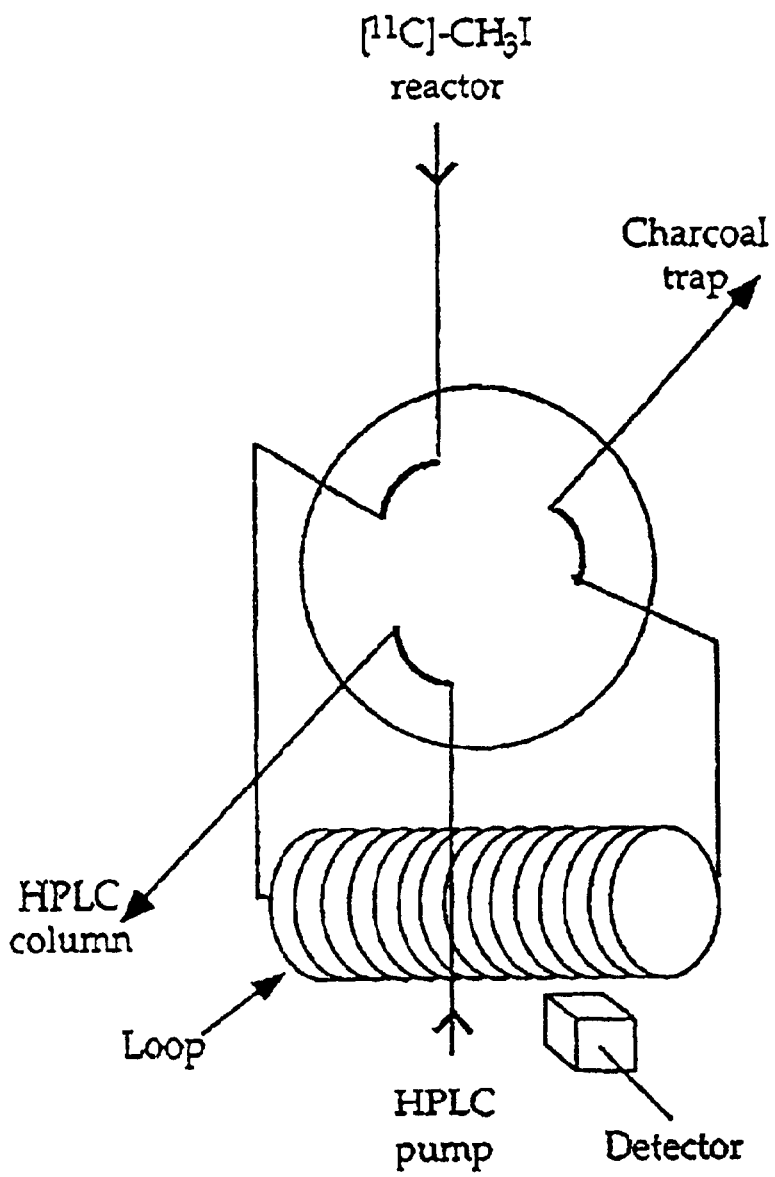
FIG. 1 is a schematic of an exemplary system and flow diagram for trapping a radiolabeling reagent in an HPLC loop coated with precursor solution, for use in the method of the invention.

The present inventors have developed a new method to radiolabel chemical compounds. Specifically the method involves the [$^{11}$C]-methylation of chemical compounds. In general terms the method involves trapping a radiolabeling reagent directly in a standard HPLC loop coated with precursor solution, allowing the reagents to react, and then directly injecting the reaction mixture onto a HPLC purification column. The method does not require the use of any additional solid support nor any heating or cooling.

The present invention therefore provides a method for radiolabeling precursor chemical compounds comprising the steps of:

injecting a sample comprising a precursor chemical compound into an injection loop of a high performance liquid chromatograph (HPLC);

injecting a radiolabeling reagent into the injection loop;

allowing the radiolabeling reagent to react with the precursor chemical compound, to provide a reaction mixture comprising a radiolabeled compound;

injecting the reaction mixture into the HPLC column; and isolating the radiolabeled compound.

The radiolabeling reagent may be any such compound that works in the method of the invention. Suitably, the radiolabeling reagent is a volatile and condensable compound. Other radiolabeling reagents that are not volatile or condensable, may be used by first dissolving in an appropriate solvent and injecting the resulting solution into a standard HPLC loop coated with precursor solution. In an embodiment of the present invention, the radiolabeling reagent is an alkylating reagent. For example, the radiolabeling may be selected from the group consisting of [$^{11}$C]-ethyl iodide, [$^{11}$C]-propyl iodide, [$^{11}$C]-methyliodide and [$^{11}$C]-acetyl iodide.

Preferably, the radiolabeling reagent is [$^{11}$C]-methyliodide. Accordingly, the present invention further provides a method for the [$^{11}$C]-methylation of precursor chemical compounds comprising the steps of:

injecting a sample comprising a precursor chemical compound into an injection loop of a high performance liquid chromatograph (HPLC);

passing [$^{11}$C]-iodomethane through the injection loop;

allowing the [$^{11}$C]-iodomethane to react with the precursor chemical compound, to provide a reaction mixture comprising a [$^{11}$C]-methylated compound;

injecting the reaction mixture into the HPLC column; and isolating the [$^{11}$C]-methylated compound.

Any precursor compound known to react in standard radiolabeling reactions, specifically [$^{11}$C]-methylation reactions, may be used in the method of the invention. Preferably the precursor chemical compound is dissolved in a suitable solvent A person skilled in the art would be able to select a suitable solvent for dissolving the precursor chemical compound based on the physical properties of this compound.

The selection of HPLC column type will be dependent on the choice of solvent and the identity of the precursor chemical compound and would be apparent to those skilled in the art. In some cases, a base and/or a catalyst may be included in the initial solution of precursor chemical compound. Suitable bases include inorganic bases such as sodium bicarbonate, sodium hydroxide and the like. Bases may be required when the precursor compound is in an acid form. Suitable catalysts include quaternary ammonium salts and the like.

Standard HPLC injection valves, loops and columns may be used with the method of the invention. An example of a standard set-up is shown in FIG. 1. The volume of solution of precursor (and base/catalyst, if necessary) applied to the loop should be designed so that the entire loop surface is coated; larger volumes may result in breakthrough of the solvent upon purging the loop with $N_2$ gas. [$^{11}$C]-iodomethane (or other volatile condensable labeling reagents) may be added to the HPLC loop coated with the solution of precursor (and base/catalyst if necessary), in a stream of nitrogen, preferably until the level of radioactivity trapped on the loop reaches a maximum. The level of radioactivity may be detected, for example, using a proximal radiation detector in the HPLC loop. In the case of [$^{11}$C]-iodomethane, and other iodinated radiolabeling reagents, a small photoiodide radiation detector positioned close to the sample loop provides the operator with information on both the amount and trapping of iodinated radiolabel inside the sample loop. The amount of time required to reach a maximum level of radioactivity in the loop will depend on the size of the loop. Once this maximum activity level is reached, the flow of nitrogen may be turned off and the chemicals allowed to react until the reaction is deemed complete, for example, about 0.5 to about 20 minutes, preferably from about 1 to about 10 minutes, most preferably from about 1 to about 5 minutes. Alternately, an aliquot of a radiolabeling reagent dissolved in an appropriate solvent may be injected into the HPLC loop coated with precursor compound (and base/catalyst if necessary) and the reagents allowed to react as described above. The contents of the loop may then injected into the HPLC column and the resulting products purified and isolated using standard procedures. The loop should be cleaned prior to use for the method of the invention. This is simply done by passing solvent, for example methanol, acetone or water (depending on the compounds used in a previous reaction), through the loop and blowing dry.

The method of the invention has been applied to the synthesis of a variety of PET pharmaceuticals (Table 1). In all cases the method was successful with results equal to or superior to those using conventional solutions in a vial methods. This includes such parameters of success such as trapping of [$^{11}$C]-iodomethane, radiochemical yield, time of synthesis, purity of final product, and specific activity. In addition to the compounds listed in Table 1 the method has been successfully applied to the [$^{11}$C]-methylation of the thiol group of (R)-(+)McNeil 5652 and the N1 of 6-chloro-1H-benzoimidazole-4-carboxylic acid (1-isobutyl-piperidin-4-ylmethyl)-amide.

In the method of the invention, [$^{11}$C]-iodomethane is trapped efficiently without cooling or the use of a solid support to increase surface area, and the methylations occur quickly, without the aid of heat. Trapping in the loop is not simply a consequence of reaction of [$^{11}$C]-iodomethane with precursor. Experiments showed that loading the loop with DMF (70 μL) with no added base or precursor also resulted in >90% trapping efficiency of the [$^{11}$C]-iodomethane.

The rate of reaction of [$^{11}$C]-iodomethane with precursor compounds at ambient temperature is fast. This compares with literature reports or other methods requiring heating, often to 90° C. for 5 min (12). Under the conditions described in Table 1, unreacted [$^{11}$C]-iodomethane accounted for less than 10% of total activity by HPLC i.e. reactions were at least 90% complete.

The versatility of the method is apparent upon examination of the variety of radiotracers synthesized (Table 1). A number of functional groups have been methylated with

[$^{11}$C]-iodomethane using this method including phenols, acids, thiols, amides, and secondary amines. Since no vials, transfer lines, cooling, heating, or sealing valves are required, no transfer losses occur, yields are high, and clean-up is minimal, this method is ideal for most radiotracers prepared using [$^{11}$C]-iodomethane.

(II) Apparatus

Figure 2:
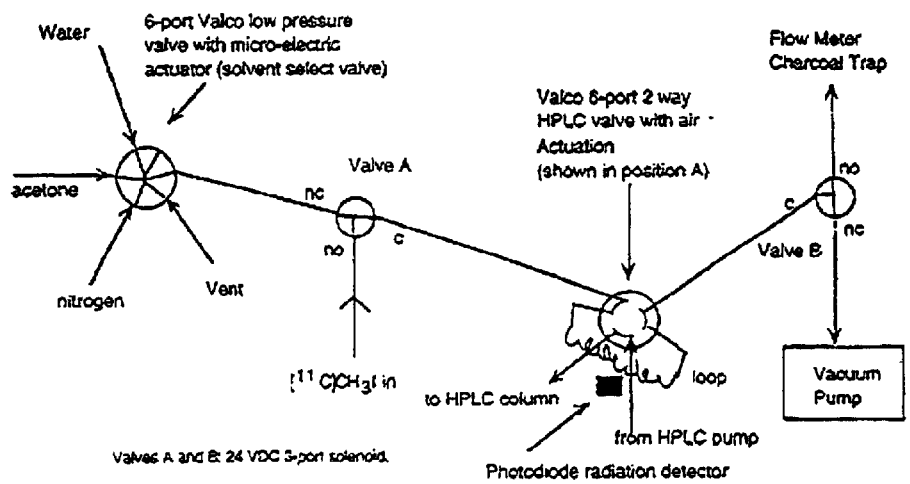
FIG. 2 is a schematic of plumbing used in an exemplary automated system for the radiolabeling reactions of the invention.

As hereinbefore mentioned, standard HPLC injection valves, loops and columns may be used with the method of the invention. An example of a standard set-up is shown in FIG. 1. FIG. 2 shows a schematic of a system for use with the method of the invention wherein three other valves (in addition to the original HPLC injection valve) have been added to allow automatic cleaning of the sample loop upon completion of the reaction. A solvent select valve allows for the sequential passage of cleaning solvent and drying gas through the loop. A small diaphragm vacuum pump may be used to suck the cleaning solvents through the system, but pressure drive solvents (either by gas or pump) will work as well.

The following non-limiting examples are illustrative of the present invention:

EXAMPLES

Methods

Precursors (normethyl) for [$^{11}$C]-methylation were synthesized in house (RTI-32, rolipram, FLB 457, DASB), or were commercially available (SCH 23390, NMS, SKF 82957). Raclopride precursor was a gift from Astra Arcus AB (Sodertaije, Sweden) and Ro 15–1788 precursor was a gift from Hoffman-LaRoche (New Jersey, USA).

General Method for Performing [$^{11}$C]-methylations in an HPLC Injection Loop (a) Set Up A commercial HPLC injection valve (Valco, Tex., USA, #AC6W) was equipped with a commercial stainless steel loop (2 mL, Valco #SL2KCW) and a commercial injection port (Valco #VISF-2). A charcoal trap was connected to the waste port of the HPLC valve and placed in a well counter to measure untapped [$^{11}$C]-iodomethane (FIG. 1). With the valve in the LOAD position, a solution of precursor, solvent, and base (if required, total volume (80 $\mu$L) was injected slowly (5–10 sec) into the clean, dry injection loop using a 100 $\mu$L gas-tight syringe (Hamilton, Nev., USA, #1810). The injection port was replaced by the [$^{11}$C]-iodomethane transfer line which had a conditioning flow of 8 mL/min N$_2$ gas passing through it. The loading of the loop with precursor solution could be made at least up to 10 min before end-of-bombardment (EOB) and no solvent emerges from the waste port. See Table 1 for specific reaction conditions.

(b) Trapping and Reaction of [$^{11}$C]-iodomethane

[$^{11}$C]-iodomethane (produced as previously described (18)) was swept into the HPLC loop coated with precursor solution by a stream of N$_2$ gas (8 mL/min) at ambient temperature. Radioactivity trapped on the loop was detected by a proximal radiation detector. When activity peaked in the loop (3–4 min), the flow of N$_2$ was stopped and the reaction allowed to proceed (1–5 min). The contents of the loop were then quantitatively injected onto the HPLC purification column by simply changing the position of the injection valve to INJECT.

(c) Cleanup

The loop had already been cleaned by the HPLC eluent. Preparation for its next run simply involved switching the valve back to the LOAD position, passing a few mL of ethanol (or water if mobile phase contains phosphate buffer) and acetone through the loop, and blowing dry.

Preparation of Raclopride Precursor (Free Base)

Raclopride precursor (HBr salt, 25.0 mg,) was dissolved in 2 mL of methanol and 1 mL of water. Aqueous sodium bicarbonate (1 N, 1.5 mL) was added and the clear solution was evaporated under vacuum to remove the methanol (no heating). The off-white precipitate was collected by filtration under vacuum and dried in a vacuum desiccator (17.87 mg, 89% yield).

The [$^{11}$C]-methylation method of the invention has been applied to the synthesis of a variety of PET radiopharmaceuticals (Table 1). In addition to the compounds listed in Table 1, the method has been successfully applied to the [$^{11}$C]-methylation of the thiol group of (R)-(+)McNeil 5652 and the N1 of 6-chloro-1H-benzoimidazole4carboxylic acid (1-isobutyl-piperidin4-ylmethyl)-amide.

The sequence of events and the state of the different components of the system for the method of the invention wherein the cleaning cycles are automated are detailed in Table 2.

Procedure

1) Stand-bye: start position in which all valves/devices are powered off or in default position. If [$^{11}$C]CH$_3$I module is being conditioned by slow nitrogen flow, then so is the HPLC sample loop. Precursor solution injected manually onto HPLC loop before synthesis. This is the only step that requires operator intervention in the hot cell.

2) Trapping: no change in valve settings but radiation detector and timer employed. Initiated upon start of [$^{11}$C]CH$_3$I distillation.

3) Reaction: no change in valve settings, simply a preset waiting time interval for the methylation reaction to proceed. Initiated either by operator or by detection of plateau of trapped radioactivity levels in HPLC loop.

4) Purification: reaction mixture injected onto HPLC column by simply switching position of HPLC valve from position A to Position B. Initiated by timer count down.

5) Clean 1: HPLC loop cleaned by sucking water through it for 60 sec. Settings are shown in the Table above. Initiated anytime after reaction mixture has been washed onto HPLC column.

6) Clean 2: HPLC loop cleaned by sucking acetone through it for 60 sec. Condition follows Clean 1 condition automatically.

7) Dry: HPLC loop dried by blowing nitrogen gas (10 psi) through it for 5 min. Condition follows Clean 2 condition automatically.

8) Stand-bye: (exit condition)

Notes a) Washing and drying times are first guess values. They work well, but shorter times may be possible if desired.

b) Only about 10 cc of wash solvents are used per run. As the solvent reservoirs hold 500 ml they need to be replenished after about 50 clean cycles.

c) A program written in Labview 5.1.1 for Windows (National Instruments, Texas) controls the module.

d) All components are commercially available except the photodiode radiation detector, which was built in house.

A person skilled in the art would know how to modify the above conditions so that radiolabeling reagents other than [11C]-methyliodide could be used.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Full Citations for References Referred to in the Specification

1. Crouzel, C., Långström, B., Pike, V. W., and Coenen, H. H. (1987) Recommendations for a practical production of [11C]methyl iodide *Appl. Radiat. Isot. Int. J. Appl. Instrum. Part A* 38, 601–603.
2. Dannals, R. F., Ravert, H. T., and Wilson, A. A. (1990) Radiochemistry of Tracers for Neurotransmitter Receptor Studies. In: *Quantitative Imaging: Neuroreceptors, Neurotransmitters, and Enzymes*. (Edited by Frost, J. J. Wagner Jr., H. N.) pp. 19–35. Raven Press, New York
3. Iwata, R., Pascali, C., Yuasa, M., Yanai, K., Takahashi, T., and Ido, T. (1992) On-line [11C]Methylation using [11C] Methyl Iodide for the Automated Preparation of 11C-Radopharmaceuticals *Appl. Radiat Isot.* 43, 1083–1088.
4. Jewett, D., Ehrenkaufer, R., and Ram, S. (1985) A Captive Solvent Method for Rapid Radiosynthesis: Application to the Synthesis of [1-11C]Palmitic Acid *Int. J. Appl. Radiat. Isot.* 36, 672–674.
5. Jewett, D. M. (1992) A Simple Synthesis of [11C]Methyl Triflate *Appl. Radiat. Isot.* 43, 1383–1385.
6. Jewett, D. M., Manger, T. J., and Watkins, G. L. (1991) Captive Solvent Methods for Fast Simple Carbon-11 Radioalkylations. In: *New Trends in Radiopharmaceutical Synthesis, Quality Assurance and Regulatory Control* (Edited by Emran, A. M.) pp. 387–391. Plenum Press, New York
7. Langer, O., Nagren, K., Dolle, F., Lundkvist, C., Sandell, J., Swahn, C.-G., Vaufrey. F., Crouzel, C., Maziere, B., and Halidin, C. (1999) Precursor Synthesis and Radiolabeling of the Dopamine D2 Receptor Ligand [11 C]Raclopride from [11C]Methyl Triflate. *J. Labelled Compd. Radiopharm.* 42, 1183–1193.
8. Långström, B., and Lundqvist, H. (1976) The preparation of 11C-methyl iodide and its use in the synthesis of 11C-methyl-L-methionine *Appl. Radiat. Isot.* 27, 357–363.
9. Larsen, P., Ulin, J., Dahistrom, K., and Jensen, M. (1997) Synthesis of [11C]Iodomethane by Iodination of [11C] Methane *Appl. Radiat. Isot* 48, 153–157.
10. Unk, J. M., Krohn, K. A., and Clark, J. C. (1997) Production of [11C]CH$_3$I by single pass reaction of [11C]CH$_4$ with I$_2$ *Nucl Med Biol* 24, 93–97.
11. Marazano, C., Maziere, M., Berger, G., and Comar, D. (1977) Synthesis of methyl iodide-11C and formaldehyde-11C *Appl. Radiat Isot* 28, 49–52.
12. Mazière, B., Coenen, H., Halldin, C., Nagren, K., and Pike, V. (1992) PET radioligands for dopamine receptors and re-uptake sites: chemistry and biochemistry *Nuc. Med. Biol.* 19, 497–512.
13. McCarron, J. A., Turton, D. R., Pike, V. W., and Poole, K. G. (1996) Remotely-controlled production of the 5-HT$_{1A}$ receptor radioligand, [carbonyl-C-11]WAY-100635, via C-11-carboxylation of an immobilized Grignard reagent *J Labelled Compds. Radiopharm.* 38, 941–953.
14. Mizuno, K. I., Yamazaki, S., Iwata, R., Pascali, C., and Ido, T. (1993) Improved Preparation of L-[Methyl-C-11] Methionine by on-Line [C-11]Methylation *Applied Radiation and Isotopes* 44, 788–790.
15. Parker, A. (1969) Protic-Dipolar Aprotic Solvent Effects on Rates of Bimolecular Reactions *Chem. Rev.* 69, 1–33.
16. Pascali, C., Iwata, R., and Ido, T. (1992) Comparative Study on the Influence of Bases on (3-N-[C-11]Methyl) Spiperone Synthesis *Int. J. Appl. Radiat. Isot.* 43, 1526–1528.
17. Watkins, G., Jewett, D., Mulholland, G., Kilbourn, M., and Toorongian, S. (1988) A Captive Solvent Method for Rapid N-[11C]Methylation of Secondary Amides: Application to the Benzodiazepine, 4'-Chlorodiazepam (RO5–4864) *Appl. Radiat. Isot.* 39, 441–444.
18. Wilson, A. A., DaSilva, J. N., and Houle, S. (1996) In vivo evaluation of (11 C] and [18F]-labelled cocaine analogues as potential dopamine transporter ligands for positron emission tomography *Nuc. Med. Biol.* 23, 141–146.
19. Wilson, A. A., DaSilva, J. N., and Houle, S. (1996) Solid-phase radiosynthesis of [11C]WAY 100635 *J. Labelled Compds. Radiopharm.* 38, 149–154.

TABLE 1

Results of using the method of the invention for the radiosynthesis of a variety of radiotracers[a].

| Compound | Yield (GBq)[b] | Specific Activity (GBq/μmole) | Base (μL) | Reaction Time (min) | precursor (mg) |
|---|---|---|---|---|---|
| RTI-32 | 11.1 | 89 | 4[c] | 1 | 0.9 |
| SCH 23390 | 8.4 | 51 | 10[d] | 5 | 1.0[e] |
| FLB 457 | 4.4 | 97 | 2[f] | 5 | 1.2 |
| NMS[g] | 10.7 | 93 | 2.5[f] | 2 | 1.0 |
| Raclopride | 5.1 | 48 | 3[h] | 5 | 1.1[i] |
| Ro 15-1788 | 13.8 | 98 | 4[c] | 2 | 0.6 |
| Rolipram | 8.1 | 81 | 3[j] | 3 | 0.3 |
| SKF 82957 | 8.1 | 84 | 10[d] | 5 | 1.0[k] |
| DASB[l] | 8.7 | 57 | n/a | 5 | 1.0 |

[a]All reactions were carried out in DMF except raclopride (DMSO). Solvent and base volume totaled 80 μL. Reported values are for a minimum of 3 runs for each radiotracer.
[b]Yields are for final formulated product, uncorrected for decay and normalized for a 15 min (40 μA) bombardment which produces 40 GBq of [11C]—CO$_2$.
[c]Tetrabutylammonium hydroxide (0.5N in methanol).
[d]Aqueous NaHCO$_3$ (1N).
[e]HCl salt.
[f]Tetrabutylammonium hydroxide (1N in methanol).
[g]N-methylspiperone
[h]5N aq. NaOH
[i]free base.
[j]Tetrabutylammonium hydroxide (0.17N in methanol)
[k]HBr salt
[l][11C]-3-amino-4-(2-dimethylaminomethyl-phenylsulfanyl)-benzonitrile.

TABLE 2

Event sequence for [11C]-methylations inside an HPLC sample loop

| Condition | Solvent Select Valve Position | Valves A & B | HPLC Valve Position | Radiation Detector | Vacuum Pump |
|---|---|---|---|---|---|
| Stand-bye | Vent | off | Position A | Off | Off |
| Trapping | Vent | off | Position A | On | Off |

TABLE 2-continued

Event sequence for [$^{11}$C]-methylations inside an HPLC sample loop

| Condition | Solvent Select Valve Position | Valves A & B | HPLC Valve Position | Radiation Detector | Vacuum Pump |
|---|---|---|---|---|---|
| Reaction | Vent | off | Position A | On | Off |
| Purification | Vent | off | Position B | On | Off |
| Clean 1 | water | on | Position A | Off | On |
| Clean 2 | acetone | on | Position A | Off | On |
| Dry | nitrogen | on | Position A | Off | Off |

We claim:

1. A method for radiolabeling precursor chemical compounds comprising:
   reacting a precursor chemical compound and a radiolabeling reagent, in an injection loop of a high performance liquid chromatograph (HPLC) without additional solid supports, to provide a reaction mixture comprising a radiolabeled compound;
   injecting the reaction mixture into the HPLC column; and
   isolating the radiolabeled compound.

2. The method according to claim 1, wherein the radiolabeling reagent is a volatile and condensable compound.

3. The method according to claim 2, wherein the radiolabeling reagent is selected from the group consisting of [$^{11}$C]-ethyl iodide, [$^{11}$C]-propyl iodide, [$^{11}$C]-methyliodide and [$^{11}$C]-acetyl iodide.

4. The method according to claim 3, wherein the radiolabeling reagent is [$^{11}$C]-methyliodide.

5. The method according to claim 1, wherein the precursor chemical compound is in the form of an acid salt and the sample further comprises a base.

6. The method according to claim 4, wherein the [$^{11}$C]-iodomethane is reacted with the precursor chemical compound for about 0.5 to about 20 minutes.

7. The method according to a claim 1, wherein the precursor chemical compound is dissolved in a solvent.

8. The method according to claim 1, wherein the sample further comprises a catalyst.

9. A method for radiolabeling precursor chemical compounds consisting essentially of:
   injecting a sample comprising a precursor chemical compound, into an injection loop of a high performance liquid chromatograph (HPLC) without additional solid supports;
   injecting a radiolabeling reagent into the injection loop;
   allowing the radiolabeling reagent to react with the precursor chemical compound, to provide a reaction mixture comprising a radiolabeled compound;
   injecting the reaction mixture into the HPLC column; and
   isolating the radiolabeled compound.

* * * * *